United States Patent [19]

Sakashita et al.

[11] Patent Number: 4,968,331

[45] Date of Patent: Nov. 6, 1990

[54] ORGANIC POLYMER SEPARATION MEMBRANE HAVING FLUORENE SKELETON AND OXYGEN ENRICHMENT DEVICE UTILIZING SAME

[75] Inventors: Masao Sakashita; Tetsuo Sakamoto; Shingo Kazama; Yoshiyuki Harada; Takero Teramoto; Kazuhiro Watanabe; Bunji Shimomura; Tsutomu Kaneta, all of Kawasaki, Japan

[73] Assignee: Nippon Steel Corporation, Tokyo, Japan

[21] Appl. No.: 492,913

[22] Filed: Mar. 13, 1990

Related U.S. Application Data

[62] Division of Ser. No. 351,720, May 15, 1989.

[51] Int. Cl.$^5$ ............... B01D 53/22; B01D 39/00; C08G 63/02

[52] U.S. Cl. .................. 55/158; 210/500.28; 528/298; 528/308

[58] Field of Search .............. 528/298, 308; 55/158; 210/500.28

[56] References Cited

U.S. PATENT DOCUMENTS

| | | | |
|---|---|---|---|
| 4,132,824 | 1/1979 | Kimura et al. | 428/220 |
| 4,143,125 | 3/1979 | Dyroff et al. | 424/48 |
| 4,192,842 | 3/1980 | Kimura et al. | 264/298 |
| 4,230,463 | 10/1980 | Henis et al. | 55/16 |
| 4,649,114 | 3/1987 | Miltenburger et al. | 435/240 |
| 4,794,159 | 12/1988 | Teramoto et al. | 528/344 |
| 4,810,771 | 3/1989 | Teramoto et al. | 528/298 |
| 4,833,214 | 5/1989 | Teramoto et al. | 525/420 |

FOREIGN PATENT DOCUMENTS

| | | |
|---|---|---|
| 0242818 | 10/1987 | European Pat. Off. |
| 55-106243 | 8/1980 | Japan |
| 60-222112 | 11/1985 | Japan |
| 62-195276 | 8/1987 | Japan |
| 2080819 | 2/1982 | United Kingdom |

OTHER PUBLICATIONS

Australian Patent Abstract AU-A-45793/85.
British Search Report, Application No. 8911213.0.

*Primary Examiner*—Morton Foelak

*Attorney, Agent, or Firm*—Kenyon & Kenyon

[57] ABSTRACT

A separation membrane consisting of a polyamide having a unit (I) or a mixing of polyamides having units (I) and (II) and (II') or a polyester having a unit (III) or (IV) and (IV') or a mixture of polyesters having unit (III) and (IV) and (IV'):

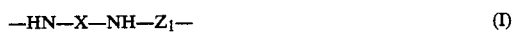

(I)

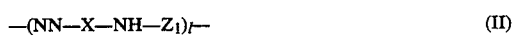

(II)

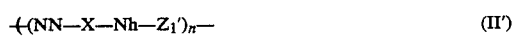

(II')

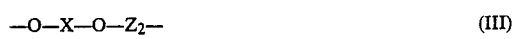

(III)

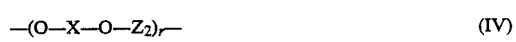

(IV)

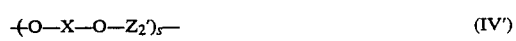

(IV')

wherein X represents

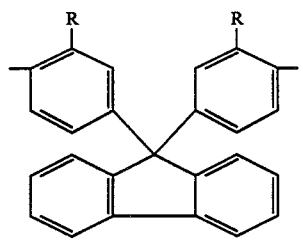

where R represents H, $CH_3$, or $C_2H_5$; $Z_1$ and $Z_2$ represent

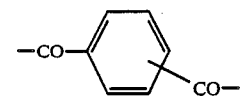

$Z_1'$ represents —CO—$(CH_2)_p$—CO—, $Z_2'$ represents —CO—CH=CH—CO—, p is an integer of 4 to 8, n/l is 1.0 to 20, and r/s is 0.5 to 100.

3 Claims, 3 Drawing Sheets 0.1mm

1μm

Fig. 4
Fig. 5
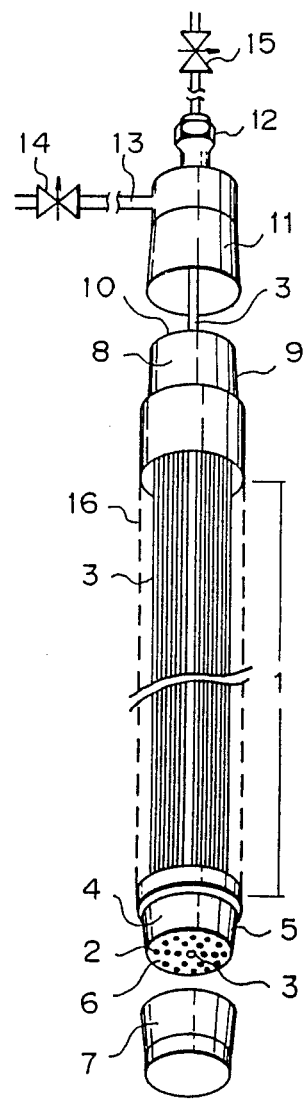
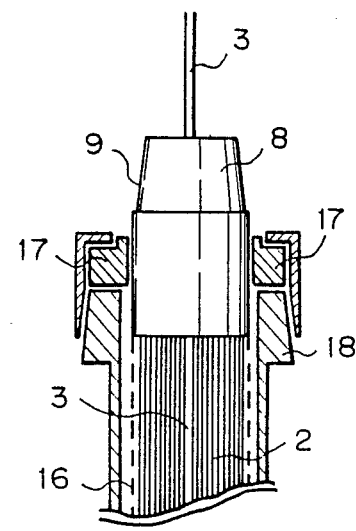

ORGANIC POLYMER SEPARATION MEMBRANE HAVING FLUORENE SKELETON AND OXYGEN ENRICHMENT DEVICE UTILIZING SAME

This is a division of application Ser. No. 07/351,720 filed May 15, 1989.

BACKGROUND OF THE INVENTION

1. Field of the Invention

The present invention relates to an organic polymer separation membrane having a fluorene skeleton. More specifically, it relates to a separation membrane having an excellent heat resistance and mechanical strength, and an oxygen enrichment device for cell culturing utilizing the membrane.

2. Description of the Related Art

Recently, separation techniques utilizing various organic polymer membranes such as a microfiltration membrane, ultrafiltration membrane, reverse osmosis membrane, and gas selective permeation membrane have been remarkably developed and some of these membranes are now practically used as an industrial scale. For example, microfiltration membranes or ultrafiltration membranes are used for the treatment of industrial waste liquids, the recovery of the waste water from buildings, and the concentration of liquid foods and reverse osmosis membranes are used for desalination of sea water.

However, the above-mentioned separation membranes have a poor heat resistance, and therefore, separation membranes for high temperature fluid is still under research and separation membranes capable of affecting a high pressure steam sterilization treatment requiring higher heat resistance have not been proposed. Regarding gas selective permeation membranes, i.e., membranes for enriching a specific gas in a gas mixture, although membrane permeation of gases having largely different molecular weights such as, for example, hydrogen gas and methane gas are being practically used, the practical use of oxygen enrichment membranes capable of obtaining air having an enriched oxygen concentration in the medical field is limited.

There are many industrial utilization fields of oxygen enriched air in which a high oxygen concentration is not necessarily required. For example, an oxygen enriched air containing 25% to 30% oxygen can be used for, for example, combustion furnaces such as blast furnaces and high temperature gas furnaces. However, in these application fields, the oxygen enriched air must be stably supplied in a large amount and at a low cost.

The technical problems to be overcome when an oxygen enriched air is obtained by a gas selective permeation membrane is how to increase the permeation flow rate per unit area of the membrane without decreasing the selective permeability. Furthermore, when a gas selective permeation membrane is practically arranged as a module, the membrane area per unit volume of module should be increased.

In addition, since there are inverse relationship between the thickness of a membrane and the permeation flow rate per unit area of the membrane, the thickness of the gas permeation membrane should be decreased. As a preparation method of such an oxygen enrichment membrane, it has been proposed to produce a composite of a thin film or membrane having a permeation or separation function and a supporting porous membrane. For example, it has been proposed in Japanese Unexamined Patent Publication (Kokai) No. 54-40868 that a gas permeation membrane having a very thin thickness (e.g., about 0.1 $\mu$m) is formed by dropwise applying, for example, an organopolysiloxane.polycarbonate copolymer solution on the surface of a liquid casting support, whereby a composite with a porous support is formed.

However, it is very difficult to prepare the above-mentioned composite membrane having a very thin separation or permeation membrane on the surface thereof, without causing any defects such as cracks and pin holes. Furthermore, the handling during the preparation of the module is trablesome and other problems also arise. Moreover, the above-mentioned siloxane type separation or permeation membranes have a disadvantageously poor heat resistance and the optimum gas permeation temperature is about 20° C. and the gas permeation or separation ratio is decreased with the increase in the temperature. For example, at a temperature of 40° C. or more, the membrane does not desirably function as an oxygen enrichment membrane.

The conventional production steps of wet process methods of preparing hollow fiber membranes generally comprise a membrane fabrication dope preparation step for dissolving the membrane base polymer in a solvent; a coagulation core liquid preparation step, an extruding step for extruding the membrane fabrication dope and the coagulation core liquid through an annular orifice and a central circular orifice of a double tubular spinning nozzle, respectively, a an air gap for sending the extruded products from the spinning nozzle to a coagulation bath through a surrounding air atmosphere (i.e., an air gap), and a coagulation step for effecting the solvent removal and coagulation. The crossectional structure of the separation or permeation membranes obtained by the above-mentioned production steps usually comprise a so-called surface dense layer (i.e., micropore layer) for determining cut-off molecular weight and a porous layer for supporting the micropores.

Attempts have been made to prepare hollow fiber separation membranes having a pore size of 0.01 $\mu$m or more and suitable for use as a ultrafiltration membrane and microfiltration membrane by appropriate production steps. However, there are still requirements for improving the adjustment or control of the size of the surface micropores and the mechanical strength of the hollow fibers. For example, as is disclosed in Japanese Unexamined Patent Publication (Kokai) No. 55-106243, polyethylene oxide is added to the membrane fabrication dope, after the membrane is fabricated, but it is still difficult to obtain the desired hollow fiber separation membrane having a uniform pore size of 0.01 $\mu$m or more. Furthermore, a hollow fiber membrane having a pore size of 0.01 $\mu$m is prepared from polysulfon as a base material by the phase separation phenomenon of the membrane fabrication dope, as disclosed in Japanese Unexamined Patent Publication (Kokai) No. 60-222112. However, the viscosity of the membrane fabrication dope is low and it is difficult to prepare hollow fiber separation membranes having a satisfactory membrane thickness. In addition, these hollow fiber separation membranes have no heat resistance sufficient to withstand against high pressure steam sterilization conditions.

On the other hand, in the growth and proliferation of animal cells, plant cells, and aerobic microorganisms in a cell culture broth in the form of a liquid or suspension, it is necessary to feed nutrient components, remove harmful metabolites, and feed oxygen, together with the provision of a solid surface corresponding to the demand of the cells, and these constitute the cell culture limiting TM factors. Accordingly, to realize an industrial bulk and high density culture of cells and microorganisms, the obstacles represented by these culture limiting factors must be removed. Further, among these limiting factors, an improvement of the feeding of oxygen is most strongly required.

The oxygen concentration in the culture broth, namely the dissolved oxygen concentration, is at a maximum at the equilibrium solubility of the oxygen, which is determined by the oxygen partial pressure in the gas phase, when a temperature and a culture broth composition are given. Nevertheless, since the cells in a culture broth constantly consume oxygen, the dissolved oxygen concentration is smaller than the equilibrium solubility, and it becomes necessary to ensure a stable feed of oxygen, for the growth and proliferation of cells.

On the other hand, the cell culturing method is intended for the growth and proliferation of only a specific cell species, and any mixing of heterologous cells of miscellaneous microorganisms must be avoided. In other words, prior to the introduction of the desired cell species, the culturing device and the culture broth must be brought to a completely sterile and organism-free state. As such a sterilization method, there are known sterilization with ethylene oxide, chemical sterilization with an aqueous hypochlorite solution, or high pressure steam sterilization. Of these sterilization methods, the high pressure steam sterilization method is industrially most preferable because washing or waste disposal after the sterilization operation is not required. Accordingly, the method of feeding oxygen into a cell culture must be based on a method which enables one of these sterilization methods, preferably the high pressure steam sterilization operation, to be used.

As the method of feeding oxygen into a culture broth, usually a bubble aeration of air from which microorganisms have been removed by a filter is employed. In this bubble aeration of air, since a dissolution of oxygen occurs at the bubble surface when rising through the liquid, fine bubbles alone must be generated in accordance with an increase of the aeration amount. Also, although it is possible to enhance the dissolved oxygen concentration by a bubble aeration of separately prepared oxygen-enriched air with a higher oxygen concentration than that of normal air, most of the enriched air will be released without dissolution, and thus this method is not industrially practical.

In cell cultivation, bubble aeration is the simplest way of feeding oxygen, wherein high pressure steam sterilization is feasible, but some problems to be solved remain, as shown hereafter. First, an excessive foaming accompanies bubble aeration. Generally, a cell culture broth is a highly viscous liquid, and bubbles introduced from the bottom of a culture vessel exist on the surface of the culture broth for a long time before collapsing, and consequently, a larger culture vessel volume is required compared with the culture broth volume. Second, cells coming into contact with the bubbles during the process of the generation of bubbles at the bottom of the culture vessel and the rise thereof through the liquid until finally collapsed, are damaged. Particularly, in animal cells in which the cell membrane has a poor mechanical strength, serious damage by contact with bubbles has been observed. Third, the bubble aeration is accompanied by a loss of the culture broth due to evaporation. This loss is considerable in the cultivation of animal and plant cells over a long term cultivation period and it becomes necessary to appropriately supplement water and the culture broth to correct the concentration of nonvolatile components contained in the culture broth and counteract a lowering of the liquid level.

As the means for solving the problems accompanying bubble aeration as mentioned above, various methods have been proposed in the prior art. For example, in Japanese Unexamined Patent Publication (Kokai) No. 62-195276, a method of carrying out cultivation while blowing a gas containing oxygen onto the culture broth surface is proposed. Such blowing gas feeding method, although having the advantage of eliminating the problems accompanying the generation of bubbles, provides a limited contact surface between the gas and the culture broth at the culture broth surface, whereby a deficiency in the amount of the gas supplied by an increase in the depth of the culture vessel occurs, and therefore, it is difficult to increase the scale of the cell cultivation.

The method of feeding oxygen over a large contact area between the gas and the culture broth, in which the generation of bubbles is inhibited, comprises diffusing a gas containing oxygen into a culture broth through a membrane dipped in the culture broth. For example, Japanese Unexamined Patent Publication (Kokai) No. 61-100190 has proposed a bubbleless gas feed method and device for feeding gas into the culture broth through a porous hollow fiber membrane not having a dense surface layer. Nevertheless, since such a porous hollow fiber membrane does not have an oxygen enrichment function, separately prepared oxygen-enriched air must be supplied to increase the amount of dissolved oxygen.

As the method of feeding gas into a culture broth by using a material having an oxygen enrichment function, Japanese Patent Publication (Kokoku) No. 60-23834 discloses a culturing method in which gas is diffused into the culture broth through a tube made of silicone rubber. But, since a thick tube is used, a high air permeation rate cannot be obtained, and thus, the gas to be fed is limited to oxygen. Also, it is difficult to increase the scale of the cell cultivation.

On the other hand, as an oxygen enrichment membrane having an excellent oxygen enrichment performance and a high gas permeation rate, Japanese Patent Publication (Kokoku) No. 59-51321 proposed a composite membrane of a polysiloxane type thin film and a porous carrier, which has been practically applied as an oxygen enrichment instrument. Although it is possible in principle to dip such a polysiloxane type oxygen enrichment film in a cell culture broth, thereby converting normal air to oxygen-enriched air and feeding gas under bubbleless conditions, due to the low heat resistance of the polysiloxane thin film, the device and the culture broth cannot be sterilized by pressurized steam in an autoclave, and therefore, it is difficult to widely utilize this method for feeding oxygen-enriched air in cell cultivation.

As apparent from the above description of the oxygen feeding means of the prior art in the cell culturing method, a gas feeding method which can enhance the dissolved oxygen concentration in the culture broth and at the same time avoid problems caused by bubble generation, and further, is industrially feasible and can be sterilized by high pressure steam, has not been proposed.

SUMMARY OF THE INVENTION

Accordingly, the objects of the present invention are to eliminate the above-mentioned problems of the prior art and to provide an aromatic condensed ring type polyamide or polyester separation membrane.

Another object of the present invention is to provide a method for preparing a microfiltration membrane, ultrafiltration membrane, or gas selective permeation membrane from the above-mentioned polyamide or polyester, suitable for use in the liquid or gas separation.

A further object of the present invention is to provide an oxygen enrichment device utilizing the above-mentioned membrane, suitable for use in, for example, cell culturing.

Other objects and advantages of the present invention will be apparent from the following description.

In accordance with the present invention, there is provided a separation membrane consisting of a polyamide having a repeating unit (I):

$$-HN-X-NH-Z_1- \quad (I)$$

wherein X represents

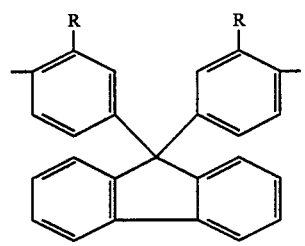

where R represents H, CH$_3$, or C$_2$H$_5$; and Z$_1$ represents the following structure:

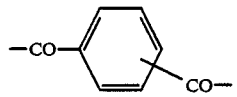

In accordance with the present invention, there is also provided a separation membrane consisting of a mixture of (i) a polyamide having a repeating unit (I):

$$-HN-X-NH-Z_{1l}- \quad (I)$$

wherein X represents

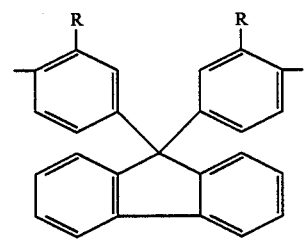

where R represents H, CH$_3$, or C$_2$H$_5$; Z$_1$ represents the following structure:

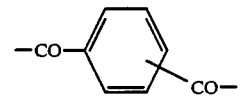

and (ii) a polyamide having units (II) and (II'):

$$-(HN-X-NH-Z_1)_l- \quad (II)$$

$$-(HN-X-NH-Z_1')_n- \quad (II')$$

wherein X and Z$_1$ are the same as defined above, Z$_1'$ represents $-CO-(CH_2)_p-CO-$, and a ratio n/l is 1.0 to 20, and p is an integer of 4 to 8: the content of the polyamide (ii) in the mixture being 50% or less.

In accordance with the present invention, there is further provided a separation membrane consisting of a polyester having a repeating unit (III):

$$-O-X-O-Z_2- \quad (III)$$

wherein X represents

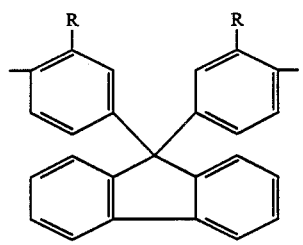

where R represents H, CH$_3$, or C$_2$H$_5$; and Z$_2$ represents the following structure:

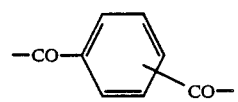

In accordance with the present invention, there is still further provided a separation membrane consisting of a polyester of (a) a unit having a repeating unit (III):

$$-O-X-O-Z_2- \quad (III)$$

wherein X represents

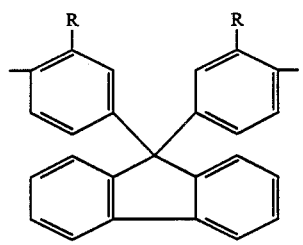

where R represents H, CH$_3$, or C$_2$H$_5$; and Z$_2$ represents the following structure:

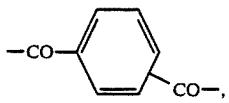

and (b) units (IV) and (IV'):

$$-(O-X-O-Z_2)_r-  \qquad (IV)$$

$$+O-X-O-Z_2')_s- \qquad (IV')$$

wherein X and $Z_2$ are the same as defined above and $Z_2'$ represents —CO—CH=CH—CO—, and a ratio r/s is 0.05 to 100.

In accordance with the present invention, there is still further provided a separation membrane consisting of a mixture of (i) a polyester having the above-mentioned unit (III) and (ii) a polyester of (a) the above-mentioned unit (III) and (b) the above-mentioned unit (IV) and (IV'). The preferable ratio of the polyesters (i)/(ii) is 95/5 to 5/95 by weight.

In accordance with the present invention, there is still further provided a method for preparing an unsymmetrically hollow fiber gas selective permeation membrane derived from the above-mentioned polyamide having a degree of polymerization such that the inherent viscosity at 30° C. under a concentration of 0.5 g/dl in N-methyl-2-pyrrolidone is 0.4 to 1.5.

In accordance with the present invention, there is still further provided a method for preparing an unsymmetrically hollow fiber gas selective permeation membrane, wherein the spinning dope contains 100 parts by weight of the polar solvent, 1 to 7 parts by weight of lithium chloride and 10 to 40 parts by weight of the above-mentioned polyamide, the spinning core liquid is water, the difference in the temperatures of the spinning dope and the spinning core liquid is within the range of ±1° C. and are between 5° C. and 35° C. and the difference in the temperature between the coagulating temperature and the spinning dope or spinning core liquid is within the range of ±5° C., whereby the nonuniformity in the micropore structure caused by the temperature difference in the spinning of the hollow fiber is minimized.

In accordance with the present invention, there is still further provided a method for preparing an unsymmetrically hollow fiber gas selective permeation membrane derived from the above-mentioned polyester having a degree of polymerization such that the inherent viscosity at 30° C. under a concentration of 0.5 g/dl in N,N-dimethylformamide is 0.5 to 1.5.

In accordance with the present invention, there is still further provided a hollow fiber separation membrane consisting of the above-mentioned polyamide, wherein the hollow fiber has a network structure over the total thickness from the inner surface to the outer surface and the inner and outer surfaces have pores having a maximum size of not less than 0.01 μm but less than 1 μm, continuously formed in the network structure.

In accordance with the present invention, there is still further provided a method for preparing the above-mentioned membrane, comprising the steps of:

extruding a membrane fabrication dope in a state of a uniform phase heated at a temperature of more than the phase transition temperature through an annular orifice of a double tubular hollow fiber spinning nozzle, while a coagulation core liquid is simultaneously extruded through a central circular orifice of the double tubular hollow fiber spinning nozzle, followed by effecting the coagulation and solvent removal by controlling at least one temperature of the temperatures of the coagulation core liquid extruded through the central circular orifice, the surrounding atmosphere from the nozzle to the outside coagulating liquid, and the outside coagulation bath to that not more than the phase transition temperature, while the phase transition of the membrane fabrication dope from the uniform phase state to the phase separated state occurs, the composition of the membrane fabrication dope having the phase transition temperature from the uniform phase state to the phase separated state and containing the above-mentioned polyamide, a good solvent for the polyamide, at least one electrolyte selected from the group consisting of univalent and bivalent cations and at least one alcohol selected from the group consisting of mono alcohols and polyols.

In accordance with the present invention, there is still further provided a liquid dipping type oxygen enrichment aeration device as shown in FIG. 4, comprising a hollow fiber oxygen enrichment membrane assembly comprising hollow fibers (2) having an oxygen enrichment capability arranged around a hollow tube (3) for an introduction of air and having a longer length than the hollow fibers, wherein both ends of the hollow fibers (2) are sealed together with the hollow tube (3) with resins (4, 8) to bonding portions (5, 9), said hollow fibers (2) and said hollow tube (3) being opened at one of the sealed bonding portions (5) to a closed vacant space (7) to form an air introducing inlet to the hollow fibers (2), said hollow fibers being opened at the other bonding portion (9) to an opened vacant space (11) having an air discharging outlet (13) connected to a pressure control valve (14) and a ground seal portion (12) to which is fixed the side face of the extending hollow tube (3), wherein the device can be dipped in a cell culture broth to effect an aeration of oxygen-enriched air through a culture broth.

In accordance with the present invention, there is still further provided a cell culturing method comprising the step of: diffusing oxygen-enriched air through a oxygen enrichment membrane consisting of the above-mentioned polyamide or polyester.

BRIEF DESCRIPTION OF THE DRAWINGS

The present invention will be better understood from the description set forth below with reference to the accompanying drawings; in which:

FIG. 4 is an elevation view of a dip type oxygen enrichment aeration devise according to the present invention; and FIG. 5 is a sectional view illustrating another example of the method of fixing the device according to the present invention.

DESCRIPTION OF THE PREFERRED EMBODIMENTS

Figure 1:
FIG. 1 is a micrograph illustrating the crosssection of a hollow fiber microfiltration membrane of polyamid according to the present invention, [i.e., R=H in the structure (I)]

As mentioned above, according to the present invention, a separation membrane consisting of a polyamide having a unit (I) or a mixture of polyamides having units (I) and (II) and (II') or a polyester having a unit (III) or (IV) and (VI') or a mixture of polyesters having units (III) and (IV) and (IV') is provided.

—NH—X—NH—$Z_1$—      (I)

—(HN—X—NH—$Z_1$)$_l$—      (II)

—(NH—X—NH—$Z_1'$)$_n$—      (II')

—O—X—O—$Z_2$—      (III)

—(O—X—O—$Z_2$)$_r$—      (IV)

—(O—X—O—$Z_2'$)$_s$—      (IV')

wherein X represents

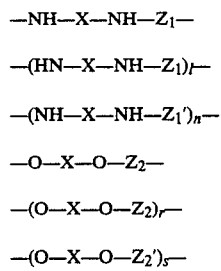

where R represents H, $CH_3$, or $C_2H_5$; $Z_1$ and $Z_2$ represent

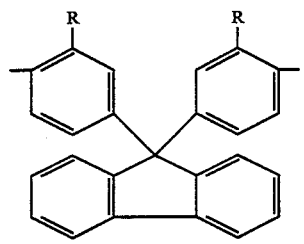

$Z_1'$ represents —CO—$(CH_2)_p$—CO—, $Z_2'$ represents —CO—CH=CH—CO—, p is an integer of 4 to 8, n/l is 1.0 to 20, and r/ is 0.05 to 100.

As is clear from the above-mentioned structures, the aromatic condensed ring structure type polyamides and polyesters according to the present invention are polymers on the basis of 9,9-bis(4-substituted phenyl) fluorene (i.e., 4-substitutions are amino in the case of the polyamides and hydroxyl in the case of the esters). Since the polyamides are hydrophilic and the polyesters are hydrophobic or water repellent, the separation membranes according to the present invention can be advantageously used depending upon the types of the materials to be separated.

As the membranes for separating a liquid from a mixture thereof, membranes having a maximum pore size of 0.01 to 1 μm and having a network structure and a micropore structure can be manufactured by utilizing a phase transition temperature of a membrane fabrication dope, as mentioned hereinbelow.

As the membranes for separating or permeating a gas from a mixture thereof, membranes having a permeation rate ratio (i.e., separation ratio) of 3 or more can be manufactured by controlling a degree of polymerization defined by the inherent viscosity of the above-mentioned polyamides and polyesters.

The above-mentioned polyamides (I) and (II) and (II') usable in the manufacture of the membranes according to the present invention can be prepared by reacting 9,9-bis (4-aminophenyl) fluorene $H_2N$—X—$NH_2$ or its derivative with, for example, terephthalic acid chloride and/or isophthalic acid chloride

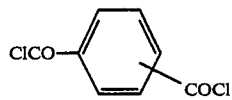

and/or a derivative thereof or a mixture of the above-mentioned acid chloride and/or a derivative thereof with adipic acid chloride ClCO—$(CH_2)_4$—COCl and/or its derivative in an inert solvent such as N,N-dimethylacrtamide or N-methyl-2-pyrrolidone under cooling for several hours. Furthermore, the terminal of the polymer of the polyamide may be preferably stabilized by, for example, a benzoyl group to prevent the discoloration of the polyamide caused by the contact thereof with air.

On the other hand, the polyesters (III) or (IV) and (IV') usable in the manufacture of the membranes according to the present invention can be prepared by reacting 9,9-bis(4-hydroxyphenyl)fluorene HO—X—OH or its derivative with, for example, terephthalic acid chloride and/or isophthalic acid chloride

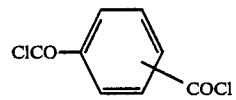

and/or a derivative thereof or a mixture of the above-mentioned acid chloride and/or a derivative thereof with fumaric acid chloride and/or maleic acid chloride ClCO—CH=CHCOCl or a mixture of the above-mentioned acid chloride in an inert solvent such as chloroolefins.

The uniform membranes or unsymmetrical membranes having a dense structure surface derived from the above-mentioned polyamides or polyesters can be advantageously utilized as a gas selective permeation membrane, especially an oxygen enrichment membrane. The porous membrane can be utilized as a ultrafiltration membrane and a microfiltration membrane having an excellent heat resistance capable of being sterilized with steam.

The polyamides usable as a base material of the present separation membrane are soluble in an aprotic polar solvent such as dimethylacetamide and N-methyl-2-pyrrolidone and the solubility thereof can be increased by adding an inorganic electrolyte such as lithium chloride. The polyesters are soluble in chloroolefins such as 1,2-dichloroethane and trichloroethane, in addition to the above-mentioned aprotic polar solvents.

The separation membranes according to the present invention may be manufactured from, as a basic material, the above-mentioned polyamide or polyester by the solvent removal of the polymer solution, for example, heat drying under a reduced pressure, or a wet process.

A flat membrane according to the present invention may be manufactured by directly casting or coating a membrane fabrication dope containing the polyamide dissolved in an appropriate solvent containing lithium chloride on a flat glass plate, and, after evaporating a portion of the solvent for a predetermined period of time, dipping the glass plate in a solvent incapable of dissolving the polymer but capable of being admissible with the solvent in the dope to effect the removal of the solvent.

Furthermore, a hollow fiber membrane may be manufactured by simultaneously extruding the above-mentioned membrane fabrication dope and a solvent incapable of dissolving the polymer (i.e., insoluble solvent) through an annular orifice and a central circular orifice of a double tubular spinning nozzle, respectively. The membranes manufactured by the above-mentioned wet processes can be utilized as a ultrafiltration membrane in a wet state.

On the other hand, the above-manufactured membranes may be advantageously utilized as a gas selective permeation membrane by drying the wet membranes. The drying may be carried out in any conventional manner, for example, by air drying at room temperature, followed by drying in vacuo or by heating at, for example, 120° C. or more.

The aromatic condensed ring type polyamides or polyesters having a fluorene skeleton according to the present invention have excellent characteristics such as a high heat resistance and excellent formability as an unsymmetrical hollow fiber membrane, and provide an excellent gas selective permeability, especially oxygen enrichment capability, without forming composite materials.

The polyamide hollow fiber gas selective permeation membranes according to the present invention may be manufactured by:

extruding a spinning dope containing the above-mentioned polyamide dissolved in an aprotic polar solvent and a spinning core liquid capable of dissolving the polar solvent but not capable of dissolving the polyamide through a annular orifice and a central circular orifice of a double tubular spinning nozzle, respectively, at an expansion ratio of 0.6 to 1.6, preferably 1.0 to 1.4 and a draft ratio of 1.0 to 2.0, preferably 1.0 to 1.2; and coagulating and solvent removing the extruded product vertically fell down from the spinning nozzle through air atmosphere in a coagulating bath, and winding the spun hollow fiber.

In the manufacture of the present polyamide hollow fiber gas selective permeation membrane, the spinning dope contains 100 parts by weight of the polar solvent, 1 to 7 parts by weight of lithium chloride and 10 to 40 parts by weight of the above-mentioned polyamide and the difference in the temperatures of the spinning dope and the spinning core liquid is within the range of ±1° C. and are between 5° C. and 35° C. and the difference in the temperature between the coagulating temperature and the spinning dope or spinning core liquid is within the range of ±5° C., whereby the nonuniformity in the micropore structure caused by the temperature difference in the spinning of the hollow fiber is minimized.

The polyamides usable in the manufacture of the unsymmetrically hollow fiber gas selective permeation membrane according to the present invention have a degree of polymerization such that the inherent viscosity at 30° C. under a concentration of 0.5 g/dl in N-methyl-2-pyrrolidone is 0.4 to 1.5, preferably 0.5 to 0.9.

Examples of the aprotic polar solvent usable in the preparation of the spinning dope are N,N-dimethylamide, N-methyl-2-pyrrolidone, and N,N-dimethylformamide or a mixture thereof. Examples of the spinning core liquid and coagulation liquid usable in the present invention are water alone, or any mixture of water with, for example, acetone, ethanol, or an aprotic polar solvent.

On the other hand, the polyester unsymmetrical gas selective permeation membrane according to the present invention may be manufactured principally in the same manner as for the manufacture of the above-mentioned polyamide membranes. The polyesters usable in the manufacture of the unsymmetrically hollow fiber gas selective permeation membrane have a degree of polymerization such that the inherent viscosity at 30° C. under a concentration of 0.5 g/dl in N,N-dimethylformamide is 0.5 to 1.5, preferably 0.5 to 1.0.

The solvents usable in the preparation of the spinning dope may include, in addition to the aprotic polar solvents, non-polar solvents such as tetrahydrofuran, 1,1,2,2-tetrachloroethane, and chloroform. When the non-polar solvents are used, acetone alone, methanol alone, ethanol alone, or any mixture thereof is used as the spinning core liquid and the coagulation liquid.

The above-mentioned polyamide and polyester unsymmetrical hollow fiber membranes according to the present invention are characterized by a multi-layer structure having a surface thin and dense gas permeation function layer having a thickness of 10 to 50 nm and an inside porous layer. Furthermore, the gas selective permeation capability of the hollow fiber membrane is improved by drying and heat treating the membrane at, for example, a temperature of 120° C. or more.

The polyamide or polyester unsymmetrical membranes according to the present invention are those having excellent heat resistance and mechanical strength. The above-mentioned dried membranes have properties suitable for use as a gas selective permeation membrane and the wet membranes have properties suitable for use as a ultrafiltration membrane. Especially, the ultrafiltration membrane of the polyamide or polyester according to the present invention is applicable to a separation of high temperature fluids and can be subjected to a high pressure steam sterilization treatment These excellent characteristics are not obtained by the conventional ultrafiltration membranes and, therefore, the present membranes may be widely utilized in a separation process of an industrial high temperature fluid, such as production of high temperature pure water, and in various separation processes in the medical industrial field requiring sterilization treatments.

The hollow fiber separation membranes consisting of the polyamide having the above-mentioned unit (I) according to the present invention are characterized in that the hollow fiber has a network structure over the total thickness from the inner surface to the outer surface and the inner and outer surfaces have pores having a maximum size of 0.05 to 1 μm, continuously formed in the network structure.

Furthermore, the hollow fiber separation membranes consisting of the polyamide having the above-mentioned units (I) and (II) and (II') according to the present invention are characterized in that the hollow fiber has a network structure over the total thickness from the inner surface to the outer surface and the inner and outer surfaces have pores having a maximum size of not less than 0.01 μm but less than 0.05 μm, continuously formed in the network structure. The mixture of the polyamides having the above-mentioned units (I) and (II) and (II') should be such that the content of the polyamide having the units (II) and (II') in the mixture being 50% by weight or less and a mole ratio n/l of the structure (II) should be 1.0 to 20.

The above-mentioned hollow fiber separation membranes can be manufactured by a conventional wet process. That is, the hollow fiber separation membrane is manufactured by:

extruding a membrane fabrication dope in a state of a uniform phase heated at a temperature of the phase transition temperature or more through an annular orifice of a double tubular hollow fiber spinning nozzle, while a coagulation core liquid is simultaneously extruded through a central circular orifice of the double tubular hollow fiber spinning nozzle, followed by effecting the coagulation and solvent removal of controlling at least one temperature, preferably two or more temperatures of the temperatures of the coagulation core liquid extruded through the central circular orifice, the surrounding atmosphere from the nozzle to the outside coagulating liquid, and the outside coagulation bath to that not more than the phase transition temperature, while the membrane fabrication dope is caused the phase transition from the uniform phase state to the phase separated state. The composition of the membrane fabrication dope is the phase transition temperature from the uniform phase state to the phase separated state and containing the polyamide having the above-mentioned unit (I) or (I) and (II) and (II'), a good solvent for the polyamide, at least one electrolyte selected from the group consisting of monovalent and divalent cations and at least one alcohol selected from the group consisting of mono alcohol (e.g., ethyl alcohol, propyl alcohol) and polyols (e.g., ethylene glycol, propylene glycol, glycerol). The phase transition temperature of the membrane fabrication dope is preferably within the range of from 10° C. to 80° C.

The polyamides having the above-mentioned units (I) or (I) and (II) and (II') usable as a base material of the hollow fiber membrane according to the present invention have excellent heat resistance. For example, the polyamide having a structure of R=H in the unit (I) has a glass transition temperature of 380° C. and a decomposition temperature of 455° C. The polyamide having a structure of R TM H and n/l of 20 in the above-mentioned units (II) and (II') has a glass transition temperature of 265° C. and a decomposition temperature of 440° C. The polyamide having a structure of R=H and n/l of 9 in the unit (II) has a glass transition temperature of 230° C. and a decomposition temperature of 415° C.

In the case of the polyamides having a structure of a mixture of the above-mentioned units (I) and (II) and (II'), the desired heat resistance of the polyamide can be maintained when the content of the unit (II) in the units (I) and (II) and (II') is 50% or less, preferably 5% to 35% and the mol ratio n/l of the repeating unit is 1 to 20, preferably 3 to 20.

As mentioned above, the hollow fiber separation membrane consisting of the polyamide according to the present invention is characterized in that the hollow fiber has a network structure over the total thickness from the inner surface to the outer surface and the inner and outer surfaces have pores having a maximum size of 0.01 to 1 μm, continuously formed in the network structure. Of these membranes, the hollow fiber separation membranes having a maximum pore size of 0.05 to 1 μm is manufactured by the polyamide having the unit (I), whereas the membrane having a maximum pore size of not less than 0.01 μm but less than 0.05 μm is manufactured by the polyamide mixture of the units (I) and (II). The polyamide having the unit (II) has an effect to decrease the size of the surface micropore of the resultant hollow fiber separation membrane.

Figure 2:
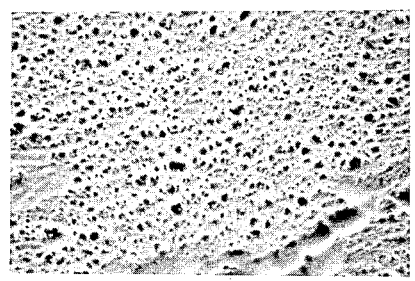
FIG. 2 is a micrograph illustrating the outer surface of the microfiltration membrane according to the present invention.

As mentioned above, FIG. 1 is a micrograph illustrating one example of the cross section of a hollow fiber separation membrane of polyamide having a structure of R=H in the above-mentioned unit [I], from which it is clearly confirmed that the network structure is present over the entire thickness from the inner surface to the outer surface. On the other hand, FIG. 2 is a micrograph illustrating the outer surface of the membrane thereof and the maximum pore size thereof is found to be about 0.2 μm. This maximum pore size range can be controlled during the manufacturing step of the hollow fiber membrane derived from, as a base material, the above-mentioned polyamide.

The network structured hollow fiber separation membranes according to the present invention can be manufactured by a wet process, the membrane fabrication dope comprises the polyamide having the unit (I) or a mixture of the units (I) and (II) and (II'), a good solvent for the polyamide, an inorganic electrolyte, and a mono alcohol or polyalcohol. Examples of the good solvent for the polyamide are polar solvents such as N,N-dimethylacetamide, N,N-dimethylformamide, N-methyl-2-pyrrolidone, dimethylsulfoxide. These polar solvents may be used alone or in any mixture thereof. In addition, the solubility of the polyamide in the solvent can be increased by dissolving, for example, LiCl, $LiNO_3$, $CaCl_2$, as an inorganic electrolyte, in the solvent. The mono alcohol or polyol is added to induce the transition of the membrane fabrication dope in the uniform phase state to the phase separation state by cooling. Examples of the monoalcohol are ethanol, propyl alcohol and cyclohexanol and examples of the polyols are ethylene glycol, propylene glycol, and glycerol. Although the composition of the membrane fabrication dope is varied depending upon the maximum pore size of the outer surface and the inner surface, generally speaking, 10 to 50 parts by weight of the polyamide, 0.5 parts to 10 parts by weight of the inorganic electrolyte, and 20 to 200 parts by weight of the mono alcohol or polyol.

As the spinning core liquid and the outside coagulating liquid for effecting the coagulation of and the solvent removal from the membrane fabrication dope, water alone or a mixed solution of water with mono alcohol such as methyl alcohol, polyol such as ethylene glycol, or good solvent such as N,N-dimethylacetamide, N-methyl-2-pyrrolidone.

The membrane fabrication dope and the spinning core liquid are extruded through an annular orifice and a central circular orifice of a double tubular hollow fiber spinning nozzle and the hollow fibers according to the present invention are manufactured in a wet process. According to the present invention, at least one temperature, preferably two or more temperatures of the temperatures of the coagulation core liquid extruded through the central circular orifice, the surrounding atmosphere from the nozzle to the outside coagulating liquid, and the outside coagulation bath is controlled to that not more than the phase transition temperature. Especially, when the temperatures of the spinning core liquid and the outside coagulation liquid are controlled to less than the phase transition temperature, the pore size in the surface of the resultant hollow fiber separation membrane can be effectively enlarged. The phase transition temperature can be determined by separately measuring the viscosity change in the temperature of the membrane fabrication dope. For example, the viscosity of a membrane fabrication dope containing the 20 parts by weight of the polyamide having a structure of R=H in the above-mentioned unit (I) and a terephthalic acid, 5 parts by weight of LiCl, and 58 parts by weight of ethylene glycol by E type viscometer. The results are shown in FIG. 3.

Figure 3:
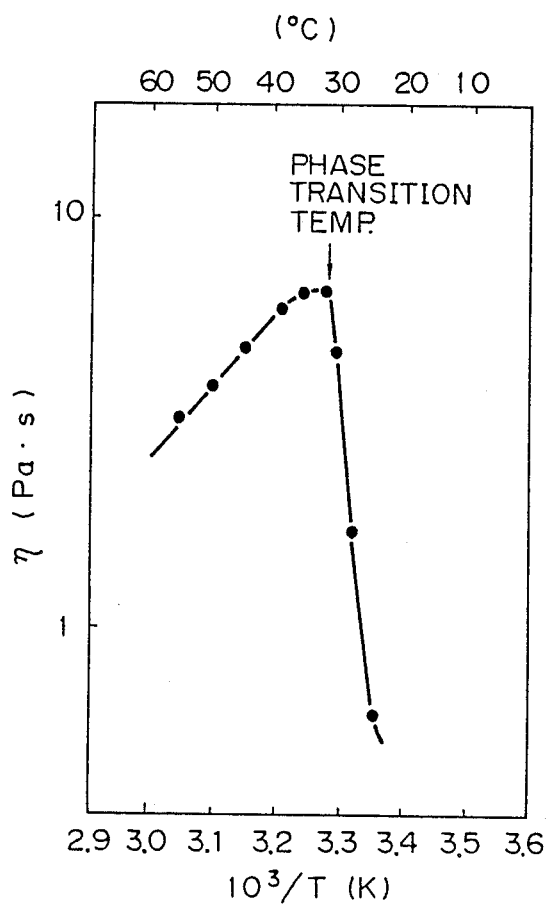
FIG. 3 illustrates a viscosity of the membrane fabrication dope of the polyamide [i.e., R=H in the structure (I)] according to the present invention.

In FIG. 3, the viscosity of the membrane fabrication dope is largely different at 32° C., and at the higher temperature side of this temperature the uniform phase state having a high viscosity and at the lower temperature side the phase separation state having a low viscosity. However, even in the phase separation state, there is a sufficiently high viscosity for the spinning of hollow fibers having a high strength, compared with the polysulfone resins having a low viscosity.

The hollow fiber separation membrane according to the present invention is extruded through the spinning nozzle coagulated and is solvent removed at temperature less than the phase transition temperature. The phase transition of not less than 10° C. is preferable to practically obtain a low temperature less than the phase transition temperature. On the other hand, the membrane fabrication dope introduced into the spinning nozzle is maintained in a uniform phase state by heating and the phase transition temperature of the membrane fabrication dope is preferably 80° C. or less, the preferable phase transition temperature range of the membrane fabrication dope is 10° C. to 80° C. The optimization of the phase transition temperature largely depends upon the kinds of the good solvent, and types and amounts of the mono alcohols or polyols In the method of preparing the present hollow fiber separation membrane, at least one member selected from N-methyl-2-pyrrolidone as a good solvent; ethylene glycol, propylene glycol, and glycerol as an additional alcohol are used. Thus, the phase transition temperature is preferably adjusted to 10 to 80° C.

The present invention provides: a liquid dipping type oxygen enrichment aeration device as shown in FIG. 4, comprising a hollow fiber oxygen enrichment membrane assembly comprised of hollow fibers (2) having an oxygen enrichment capability arranged around a hollow tube (3) for an introduction of air and having a longer length than the hollow fibers, with both ends of the hollow fibers (2) being sealed together with the hollow tube (3) with resins (4, 8) to bonding portions (5, 9), the hollow fibers (2) and the hollow tube (3) being opened at one of the sealed bonding portions (5) to a closed vacant space (7) to form an air introducing inlet to the hollow fibers (2), the hollow fibers being opened at the other bonding portion (9) to an opened vacant space (11) having an air discharge outlet (13) connected to a pressure control valve (14) and a ground seal portion (12) to which is fixed the side face of the extending hollow tube (3), characterized in that the device can be dipped in a cell culture broth to effect aeration of oxygen-enriched air through the culture broth.

In the above liquid dipping type oxygen enrichment aeration device, the hollow fibers (2) having an oxygen enrichment capability and the hollow tube for an introduction of air are sealed with the resins (4, 8) at both ends of the hollow fibers, and further, the hollow fibers as a whole are positioned within a porous tubular body having pore diameters of 0.05 μm or more, whereby the hollow fibers are protected from direct contact with the culture broth fluid, and oxygen-enriched air can be aerated through the fine pores of the porous tubular body into the culture broth; and Further in the above liquid dipping type oxygen enrichment aeration device the hollow fibers having an oxygen enrichment capability comprise the base material of a polyamide represented by the formula (A) or a polyester represented by the formula (B):

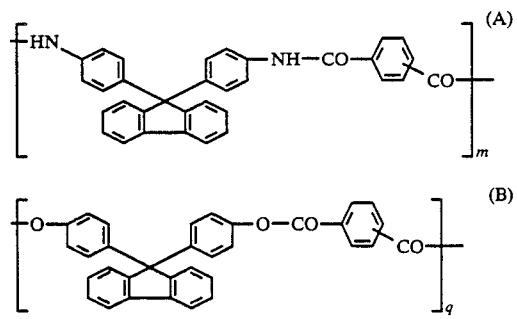

wherein m and q represent the number of repeating units.

Referring now to the accompanying drawings, the liquid dip type oxygen enrichment aeration device is described in more detail.

The hollow fibers having an oxygen enrichment capability to be used in the present invention are characterized in that they comprise a polyamide represented by the formula (A) or a polyester represented by the formula (B) as mentioned above as the base material, and are spun by the wet process into fibers having outer diameters of 3 to 0.1 mm, inner diameters of 2.8 to 0.05 mm, and an excellent heat resistance high enough that the oxygen enrichment capability will not be deteriorated by a steam sterilizing operation at, for example, 127° C.

In the present device, the hollow tube for an introduction of air also functions as the center shaft, and a base material thereof is not particularly designated, provided that it has a mechanical strength and heat resistance which can maintain the structure of the present device, and can be adhered to the resin as described below. In this case, a non-corrosive metal tube such as stainless steel tube is preferably used, and a thin stainless tube with an outer diameter of ¼ inch or less will have a mechanical strength sufficient to maintain the structure, and further, allow the present device to be deformed as desired into a spiral shape within the cultivation tank, and therefore is optimally used as the hollow tube.

Up to several thousand oxygen enrichment hollow fibers are arranged around one hollow tube having a longer length than the fibers, and both ends of the hollow fibers and the hollow tube are sealed to form bonding portions. As the resin for sealing, embedding materials having an excellent mechanical hardness and heat resistance, for example, epoxy type curable resins may be employed, and as the bonding member, the resin itself for sealing other heat-resistant resins or bonding members made of metal ca be used. At the bonding portion, which becomes the air introduction inlet into the hollow fibers, namely the end of the bonding portion (5) in FIG. 4, the hollow fibers are open to form an open face (6), and the open face of the hollow tube may be on the same level as this or alternately recessed or protruded, as desired.

The manner in which the bonding portion (5) and the closed vacant space portion (7), and the bonding portion (9) and the opened vacant space portion (11) are bonded is not particularly designated, provided that a pressure resistance of 10 kg/cm² is obtained and that dismantling is easy, but most preferably a tapered screw used. Also, for bonding between the hollow tube extending through the hollow fiber opened face (10) in the bonding portion (9), and the opened vacant space portion (11), an O-ring may be employed, which is a bonding system in which the vacant space portion (11) and the hollow fibers portion are separable from each other.

The hollow fibers at the permeation portion (1) for oxygen-enriched air between the both bonded portions of the hollow fibers are in contact with the culture broth, thereby aerating oxygen-enriched air into the broth, but the hollow fibers as a whole may be also positioned within a porous tubular body to protect the hollow fibers from direct contact with the culture broth fluid under stirring, thereby effecting the aeration through fine pores of the porous tubular body.

For such a porous tubular body, a porous tube made of a fluorine resin is optimum, due to the lightweight and shape deformability thereof, but a metal tube or a ceramic tube also may be used, and for either material, a porous tubular body having a fine diameter of 0.05 μm or more, preferably 0.2 μm to 10 μm, with a bubbling pressure of the oxygen-enriched air passing through the liquid of 1 atm. or less, preferably 0.5 atm. or less, may be employed.

The liquid dipping type oxygen enrichment aeration device is characterized in that hollow fibers having an oxygen enrichment capability are dipped in a culture broth to enhance the dissolved oxygen concentration in the culture broth, thereby enabling a high density cultivation of cells and an alleviation of the problems accompanying bubble generation. When the present device is fixed in the culturing tank to be used for aeration of oxygen-enriched air into the culture broth, the portion between the bonding portion (9) and the vacant space portion (7) is located within the culture tank.

A diversity of methods may be used for fixing the culturing tank to the bonding portion (9), depending on the volume and the shape of the culturing tank, and the bonding portion must be worked in accordance with such demands, but in the case of a small scale culturing tank for research and development or an intermediate plant with a volume of 10 liters or less, the bonding portion can be easily fixed through a silicone rubber packing onto the instrument setting opening at the upper portion of the culturing tank without particular working. FIG. 5 illustrates a method of fixing the branched pipe (18) for an instrument setting of a small culturing tank, by using a silicone rubber packing (17).

With an increase of the amount of culture broth, the number of hollow fibers necessary for oxygen enrichment aeration is necessarily increased, and consequently, the fixed portion with the culturing tank must be firm. This problem is easily solved by previously imparting the fixing system of the culturing tank to the structure of the bonding portion (9). For example, when the clamping method by an O-ring is employed, a liquid dipping type oxygen enrichment aeration device with an opening portion diameter of 50 mm or more, having a bundle of some thousand hollow fibers, can be formed.

EXAMPLES

The present invention will now be further illustrated by, but is by no means limited to, the following Examples and Comparative Examples, wherein all parts and percentages are expressed on a weight basis unless otherwise noted.

In the following Examples and Comparative Examples, the inherent viscosity of the polyamide or polyester to be used as a base material for the membranes was determined by dividing the logarithm value of a relative viscosity of the polyamide or polyester by the concentration. The relative viscosity was measured at a concentration of 0.5 g/dl at 30° C. The solvent used was N-methyl-2-pyrrolidone for the polyamide and N,N-dimethylformamide for the polyester. The viscosity was measured by an Ostwald viscometer.

Furthermore, an oxygen permeation rate $Q_{O2}$ and a separation ratio α representing an oxygen enrichment performance of the hollow fiber oxygen enrichment membrane were calculated as follows. That is, a small oxygen enrichment test unit having a number of the hollow fiber of 20 and an effective length of 10 cm was arranged. The effective area of the membrane is assumed to be S. An artificial air having an oxygen concentration of 21% (argon was removed) under a pressure of p was introduced into the inside of the hollow fiber and a rate $J_{air}$ of an oxygen enrichment air permeated from the inside of the hollow fiber membrane to the outside of the hollow fiber membrane opened to 1 atm atmosphere and mole fractions $X_{O2}$ and $X_{N2}$ of oxygen and nitrogen are measured. The $Q_{O2}$, $Q_{N2}$, and α are calculated as follows:

$$Q_{O2} = J_{air} \cdot X_{O2}/S \ (0.21 \times p - X_{O2})$$

$$Q_{N2} = J_{air} \cdot X_{N2}/S \ (0.79 \times p - X_{N2})$$

$$\alpha = Q_{O2}/Q_{N2}$$

The $Q_{O2}$ and $Q_{N2}$ in the Examples are all determined at 40° C. and the unit is Nm³/m² hr.atm.

EXAMPLE 1

Polyamides having a repeating unit (A-1);

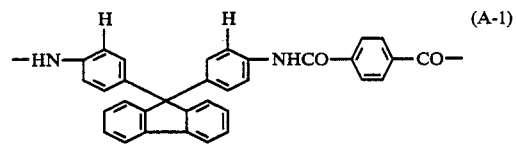

and an inherent viscosity of 0.5 to 0.9 were used for the evaluation of the permeation coefficient P (Nm³·m/m²·hr·atm) for oxygen and nitrogen. Sheet-like membranes having a thickness of 20 μm were prepared from a N,N-dimethylacetamide solution of the polyamide at 40° C. The gas permeation coefficient was determined as follows. That is, a polyamide in N,N-dimethylacetamide solution was coated on a flat glass plate by a doctor blade, followed by drying the product at 150° C. under a reduced pressure. Thus, the sheet-like membrane having a thickness of 20 μm was obtained. The gas permeation constant was calculated in which one end of the membrane is pressurized under such conditioned that one end of the sheet-like membrane having a thickness of 20 μm was pressurized to 2 atm and the other end was maintained at 1 atm.

The results are shown in Table 1.

TABLE 1

| Polyamide Inherent viscosity (dl/g) | Permeation Coefficient (Nm$^3 \cdot$ m$^2$/m$^2 \cdot$ hr $\cdot$ atm) | | Ratio of permeation coefficient $P_{O2}/P_{N2}$ |
|---|---|---|---|
| | $P_{O2}$ | $P_{N2}$ | |
| 0.55 | $1.1 \times 10^{-8}$ | $2 \times 10^{-9}$ | 5.5 |
| 0.77 | $9.5 \times 10^{-9}$ | $1.7 \times 10^{-9}$ | 5.7 |
| 0.87 | $8.5 \times 10^{-9}$ | $15 \times 10^{-9}$ | 5.8 |

EXAMPLE 2

The gas permeation coefficient at 40° C. of various polyesters having a repeating unit:

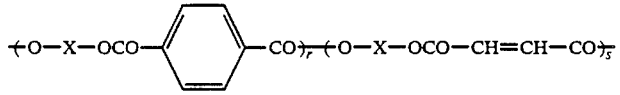

wherein X is as defined above and r/n is 0.05, 0.25, 1, 4, and 99, and having an inherent viscosity of 1.0 dl/g were determined in the same manner as in Example 1, except that 1,1,2,2-tetrachloroethlane was used, as a solvent, instead of N,N-dimethylacetamide. The membrane in the form of a sheet having a thickness of 20 μm was prepared by casting and drying from the 1,1,2,2-tetrachloroethane solution.

The results are shown in Table 2.

TABLE 2

| | Permeation Coefficient (Nm$^3 \cdot$ m/m$^2 \cdot$ hr $\cdot$ atm) | | Ratio of Permeation Coefficient |
|---|---|---|---|
| r/n | $P_{O2}$ | $P_{N2}$ | $P_{O2}/P_{N2}$ |
| 0.05 | $3.8 \times 10^{-8}$ | $8.2 \times 10^{-9}$ | 4.6 |
| 0.25 | $3.5 \times 10^{-8}$ | $7.7 \times 10^{-9}$ | 4.6 |
| 1 | $3.0 \times 10^{-8}$ | $6.6 \times 10^{-9}$ | 4.5 |
| 4 | $2.6 \times 10^{-8}$ | $5.2 \times 10^{-9}$ | 5.0 |
| 99 | $6 \times 10^{-9}$ | $1.1 \times 10^{-9}$ | 5.5 |

EXAMPLE 3

The gas permeation coefficients at 40° C. of various polyesters having a repeating unit:

wherein X is as defined above and l/n is 4 and 1, and having an inherent viscosity of 0.8 dl/g, were determined in the same manner as in Example 1, except that 1,1,2,2-tetrachloroethane was used as a solvent instead of N,N-dimethylacetamide. The membrane in the form of a sheet having a thickness of 20 μm was prepared by casting and drying from the 1,1,2,2-tetrachloroethane solution.

The results are shown in Table 3.

TABLE 3

| | Permeation Coefficient (Nm$^3 \cdot$ m/m$^2 \cdot$ hr $\cdot$ atm) | | Ratio of Permeation Coefficient |
|---|---|---|---|
| l/n | $P_{O2}$ | $P_{N2}$ | $P_{O2}/P_{N2}$ |
| 4 | $3.0 \times 10^{-8}$ | $7.0 \times 10^{-9}$ | 4.3 |
| 1 | $4.5 \times 10^{-8}$ | $1.1 \times 10^{-8}$ | 4.0 |

EXAMPLES 4 to 14

Polyamides having the unit (A-1) and having an inherent viscosity of 0.5 to 0.9 were dissolved in 100 parts of N,N-dimethylacetamide containing 5 parts of lithium chloride previously dissolved therein. This solution was used as a spinning dope and water alone was used as a spinning core liquid, and the hollow fiber oxygen enrichment membrane was spun therefrom. The distance between the spinning nozzle and the coagulation bath (i.e., air gap distance) was 40 cm.

The spinning conditions and the oxygen enrichment performance are shown in Table 4.

As is clear from the results in Table 4, the hollow fiber oxygen enrichment membranes obtained from the above-mentioned polyamides having an inherent viscosity of 0.5 to 0.9 exhibit an oxygen enrichment performance of a separation ratio of 3 or more.

TABLE 4

| Example No. | Inherent viscosity of polyamide (dl/g) | Concentration of spinning dope* | Temp. °C. | | Draft ratio | Expansion ratio | Permeation rate (Nm$^3$/m$^2 \cdot$ hr $\cdot$ atm) | | Separation ratio |
|---|---|---|---|---|---|---|---|---|---|
| | | | Spinning dope | Coagulation liquid | | | $Q_{O2} \times 10^2$ | $Q_{N2} \times 10^2$ | |
| 4 | 0.55 | 27.0 | 5 | 5 | 1.0 | 1.0 | 2.7 | 0.67 | 4.0 |
| 5 | 0.65 | 21.0 | 20 | 20 | 1.0 | 1.0 | 4.9 | 1.17 | 4.5 |
| 6 | 0.77 | 18.5 | 20 | 20 | 1.0 | 0.8 | 3.3 | 0.85 | 3.9 |
| 7 | 0.77 | 18.5 | 20 | 20 | 1.0 | 1.0 | 3.6 | 0.91 | 4.0 |
| 8 | 0.77 | 18.5 | 20 | 20 | 1.0 | 1.2 | 3.9 | 0.90 | 4.3 |
| 9 | 0.77 | 18.5 | 20 | 20 | 1.0 | 1.4 | 5.0 | 1.70 | 3.0 |
| 10 | 0.77 | 18.5 | 20 | 20 | 1.2 | 1.0 | 6.7 | 2.10 | 3.3 |
| 11 | 0.77 | 21.0 | 20 | 20 | 1.0 | 1.0 | 2.6 | 0.62 | 4.2 |
| 12 | 0.77 | 16.0 | 30 | 30 | 1.0 | 1.0 | 8.7 | 2.90 | 3.0 |
| 13 | 0.77 | 16.0 | 5 | 10 | 1.0 | 1.0 | 2.5 | 0.59 | 4.2 |
| 14 | 0.87 | 17.5 | 20 | 20 | 1.0 | 1.0 | 11.4 | 3.80 | 3.0 |

TABLE 4-continued

| Example No. | Inherent viscosity of polyamide (dl/g) | Concentration of spinning dope* | Temp. °C. Spinning dope | Temp. °C. Coagulation liquid | Draft ratio | Expansion ratio | Permeation rate $Q_{O2} \times 10^2$ ($Nm^3/m^2 \cdot hr \cdot atm$) | Permeation rate $Q_{N2} \times 10^2$ ($Nm^3/m^2 \cdot hr \cdot atm$) | Separation ratio |
|---|---|---|---|---|---|---|---|---|---|
| 15 | 0.87 | 20.0 | 20 | 20 | 2.0 | 0.8 | 8.5 | 2.66 | 3.2 |

*Parts by weight of polyamide dissolved in 100 parts by weight of solvent

COMPARATIVE EXAMPLES 1 AND 2

The hollow fiber was spun from the polyamide having an inherent viscosity of 0.36 or 1.7 in the same manner as in Examples 4 to 14.

The spinning conditions and oxygen enrichment performances are shown in Table 5.

As is clear from the results shown in Table 5, the hollow fiber membrane obtained from a base polyamide having an inherent viscosity of a lower or higher inherent viscosity does not exhibit an excellent oxygen enrichment performance.

TABLE 5

| Comparative Example | Inherent viscosity of polyamide (dl/g) | Concentration of spinning dope* | Temp. °C. Spinning dope | Temp. °C. Coagulation liquid | Draft ratio | Expansion ratio | Permeation rate $Q_{O2} \times 10^2$ ($Nm^3/m^2 \cdot hr \cdot atm$) | Permeation rate $Q_{N2} \times 10^2$ ($Nm^3/m^2 \cdot hr \cdot atm$) | Separation ratio |
|---|---|---|---|---|---|---|---|---|---|
| 1 | 0.36 | 40 | 5 | 5 | 1.0 | 1.0 | 15.0 | 13.0 | 1.2 |
| 2 | 1.70 | 12 | 20 | 20 | 1.0 | 1.2 | 23.0 | 23.0 | 1.0 |

EXAMPLE 15

The permeation rate of pure water, cut-off molecular weight of dextran and burst strength of the wet hollow fiber membrane of Example 4 before the drying treatment are shown in Table 6, where the characteristics were measured at 25°, 45°, and 83° C. The burst strength represents a bursting pressure when pure water is pressurized into the inside of the hollow fiber one end which of is sealed.

TABLE 6

| Temp. (°C.) | Permeation rate of pure water ($l/m^2 \cdot hr \cdot (kgcm^{-2})$) | Cut-off molecular weight | Bursting strength ($kgcm^{-2}$) |
|---|---|---|---|
| 25 | 45 | 7000 | 25 |
| 45 | 88 | 8000 | 24 |
| 83 | 155 | 10000 | 23 |

As is Clear from the results shown in Table 6, the heat resistance of the wet membrane of the polyamide having the repeating unit (A-1) shown in Example 1 is excellent and the cut-off molecular weights and burst strengths at 83° C. and 25° C. are substantially identical. Furthermore, the increase in the permeation rate of pure water with the temperature is caused by the decrease in the viscosity of water.

EXAMPLE 16

The same hollow fiber membrane as in Example 15 was subjected to a high pressure steam sterilization treatment at a temperature of 121° C. and under a pressure of 1.2 atm. The permeation rate of pure water was 30 liter/$m^3 \cdot hr \cdot kg \cdot cm^{-2}$, a cut-off molecular weight of 6000, and a burst strength of 25 $kg \cdot cm^{-2}$, which are similar to those of Example 15 at 25° C.

EXAMPLE 17

Hollow fiber membranes were obtained from a copolyamide having a repeating unit (A-1) in Example 1 and the following repeating unit (B-1) at a mole ratio (A-1):(B-1)=50:50 in the same manner as in Example 15.

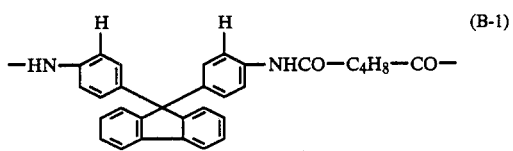

The permeation rate of pure water, cut-off molecular weight and burst strength of the resultant membrane were determined and the results are shown in Table 7.

TABLE 7

| Temp. (°C.) | Permeation rate of pure water ($l/m^2 \cdot hr \cdot (kgcm^{-2})$) | Cut-off molecular weight | Burst strength ($kgcm^{-2}$) |
|---|---|---|---|
| 25 | 80 | 30000 | 22 |
| 45 | 150 | 35000 | 21 |
| 83 | 250 | 40000 | 19 |

EXAMPLE 18

Hollow fiber membranes were prepared in the same manner as in Example 17 except that copolyamides having a mole ratio of (A-1):(B-1)=10:90 and 5:95 were used as a base material.

The permeation rate of pure water, cut-off molecular weight and burst strength of the resultant membrane were determined and the results are shown in Table 8.

TABLE 8

| Mole ratio (A-1):(B-1) | Temp. (°C.) | Permeation rate of pure water ($l/m^2 \cdot hr \cdot (kgcm^{-2})$) | Cut-off molecular weight | Burst strength ($kgcm^{-2}$) |
|---|---|---|---|---|
| 10:90 | 25 | 120 | 75000 | 10 |
| 10:90 | 45 | 180 | 80000 | 10 |
| 10:90 | 83 | 300 | 100000 | 8 |
| 5:95 | 25 | 150 | 100000 | 10 |

EXAMPLE 19

A porous membrane obtained from a polyester having a repeating unit:

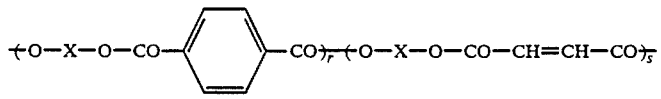

and having micropores such that polyethylene glycol having a molecular weight of 4000 is permeated therethrough was heat treated at 300° C. for 30 minutes to make the porous membrane insoluble in solvents. The same polyester in 1,1,2,2-tetrachlorcethane solution at a concentration of 10% was uniformly coated on the resultant heat treated porous membrane to obtain a composite membrane with a uniform polyester membrane having a thickness of about 1 μm.

The permeation rate Q of oxygen and nitrogen at 25° C. under a humidity of 0% and 40% and the separation ratio are shown in Table 9.

As is clear from the results shown in Table 9, the decrease in the separation ratio is reduced even in wet air.

TABLE 9

| Relative humidity (%) | Permeation rate (Nm³/m² · hr · atm) | | Separation ratio |
|---|---|---|---|
| | $Q_{O2} \times 10^2$ | $Q_{N2} \times 10^2$ | |
| 0 | 1.6 | 0.30 | 5.3 |
| 40 | 1.4 | 0.28 | 5.0 |

EXAMPLE 20

The composite separation membrane obtained in Example 19 was further insolubilized in solvents by heat treating the membrane at 280° C. for 30 minutes. The permeation rates of oxygen and nitrogen at 40° C. were determined when pressurized air was applied to the uniform membrane side of the composite membrane and 40% aqueous ethanol solution was applied to the porous support membrane side.

As a result, $Q_{O2}$ was $8.2 \times 10^{-2}$ Nm³/m²·hr·atm and $Q_{N2}$ was $1.9 \times 10^{-2}$ Nm³/m²·hr·atm and the separation ratio was 4.3. The composite membrane according to the present invention allows an oxygen enrichment air to be directly introduced into a liquid medium.

EXAMPLE 21

A membrane fabrication dope was prepared by dissolving, in 100 parts by N-methyl-2-pyrrolidone (NMP), 5 parts of lithium chloride, 20 parts of polyamide having above-mentioned repeating unit (A-1), and 58 parts of ethylene glycol (EG). The phase transition temperature of this dope is 32° C. from the viscosity change thereof with temperature (FIG. 3).

The resultant dope was heated to 40° C. and was extruded through an annular orifice (outer diameter=1 mm, inner diameter=0.8 mm) of the spinning nozzle and, simultaneously, a spinning core liquid obtained by dissolving 185 parts of NMP in 100 parts of water was extruded at 5° C. through a central circular orifice (inner diameter =0.6 mm). The extrudate vertically fell down through the surrounding air atmosphere at 25° C. to an outside coagulation liquid (i.e., water alone) at 5° C. to effect the coagulation and the removal of solvent. Thus, the hollow fiber separation membrane having an outer diameter of 1.0 mm and an inner diameter of 0.7 mm was obtained. The phase transition temperature of the membrane fabrication dope was determined by an E type viscometer at a temperature decrease rate of 0.5° C./min. The sizes of the pores in the inner and outer surfaces of the hollow fiber separation membrane were determined from photographs of a scanning electron microscope. The permeation rate of pure water through the hollow fiber separation membrane was determined at an operating pressure of 1.0 kg/cm² and a temperature of 25° C. The resultant hollow fiber membrane i.e., microfiltration membrane, is composed of a network structure entirely from the inner surface to the outer surface (FIG. 1) and micropores are continuously opened over the network structure. The maximum pore sizes were 0.1 μm in the inner surface and 0.2 μm in the outer surface (FIG. 2). The water permeation rate was 1.050 liter/m²·hr·atm.

The membrane fabrication conditions and the performances of the hollow fiber are shown in Table 10.

EXAMPLES 22-26

Hollow fiber separation membranes having an outer diameter of 1.0 mm and an inner diameter of 0.7 mm were obtained under the conditions listed in Table 10 by using a membrane fabrication dope obtained by dissolving 5 parts of lithium chloride, 15-20 parts of polyamide having the same repeating unit as in Example 21, EG, propylene glycol (PG), or Glycerol (Gly) as a polyol. The characteristics of the resultant hollow fiber separation membrane (i.e., microfiltration membrane) are also shown in Table 10.

The pore sizes of the inner and outer surfaces in the hollow fiber separation membrane can be controlled to 0.05 to 1 μm by the kinds of the polyols added and the concentration thereof.

EXAMPLES 27 AND 28

Hollow fiber separation membrane having an outer diameter of 1.0 mm and an inner diameter of 0.7 mm were obtained in the same manner as in Example 21, except that membrane fabrication dopes obtained by dissolving, in 100 parts of NMP, 5 parts of lithium chloride, 20 parts of polyamide mixture composed of a repeating units of the above-mentioned units (A-1) and the following unit (C-1),

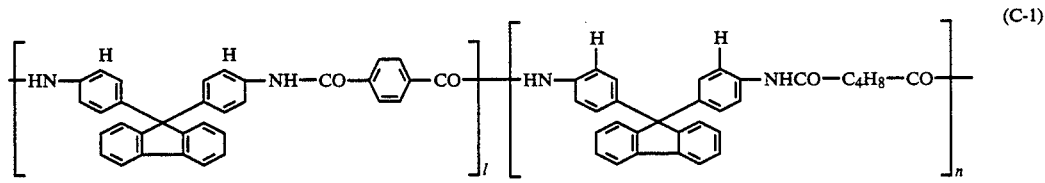

and the mol ratio of n/l of 9.0, and EG as a polyol. The membrane manufacturing conditions and the characteristics of the resultant hollow fiber separation membranes are also shown in Table 10.

EXAMPLES 31 TO 34

Hollow fiber oxygen enrichment membranes having an outer diameter of 0.7 mm and an inner diameter of

TABLE 10

| Example | Polyamide (parts) | | Alcohol (parts) | | Phase transition temp. (°C.) | Dope temp. (°C.) | NMP in core liquid (parts) | Core liq. temp. (°C.) | Air run temp. (°C.) | Outside coagulation liq. temp. (°C.) | Maximum pore size in inner surface (μm) | Maximum pore size in outer surface (μm) | Water permeation rate l/m²·hr·atm |
|---|---|---|---|---|---|---|---|---|---|---|---|---|---|
| 21 | A-1 | 20 | EG | 58 | 32 | 40 | 186 | 5 | 25 | 5 | 0.1 | 0.2 | 1,050 |
| 22 | A-1 | 20 | EG | 58 | 32 | 40 | 186 | 5 | 5 | 5 | 0.1 | 0.2 | 900 |
| 23 | A-1 | 20 | EG | 62 | 53 | 60 | 66 | 5 | 25 | 5 | 0.5 | 1 | 2,500 |
| 24 | A-1 | 20 | EG | 58 | 32 | 40 | 186 | 5 | 25 | 5 | 0.3 | 0.5 | 1,500 |
| 25 | A-1 | 20 | PG | 79 | 40 | 45 | 186 | 5 | 25 | 5 | 0.05 | 0.08 | 220 |
| 26 | A-1 | 20 | Gly | 39 | 39 | 45 | 186 | 5 | 25 | 5 | 0.05 | 0.05 | 125 |
| 27 | A-1 C-1 | 18 2 | EG | 55 | 30 | 40 | 186 | 5 | 25 | 5 | 0.03 | 0.05 | 400 |
| 28 | A-1 C-1 | 15 5 | EG | 53 | 25 | 30 | 186 | 5 | 25 | 5 | 0.01 | 0.02 | 320 |

EG: Ethylene glycol
GP: Propylene glycol
Gly: Glycerol

EXAMPLE 29

The hollow fiber microfiltration membranes of Examples 21 and 28 were subjected to high pressure steam treatment at 123° C. for 30 minutes. The characteristics of the resultant hollow fiber membranes were evaluated. As a result, the maximum pore sizes of the inner and outer surfaces of the hollow fiber membrane of Example 21 were not changed at 0.1 μm and 0.2 μm, respectively and the water permeation rate was 1020 liter/m²·hr·atm. The treated hollow fiber membrane of Example 28 also exhibited unchanged maximum pore sizes of the inner and outer surfaces of the membrane and the water permeation rate was 300 liter/m²·hr·atm.

Thus, the characteristics of the present hollow fiber microfiltration membrane, were not deteriorated by the high pressure steam sterilization treatment.

EXAMPLE 30

A nonporous membrane in the form of a sheet having a thickness of 20 μm obtained from a polyamide having the above-mentioned structure (A-1) or a polyester having R=H in the unit (III) was assembled as an oxygen enrichment device having a membrane area of 20 cm². This device was dipped in an MS culture medium used in the plant cell culturing. When ambient air was introduced, after pressurizing at 2 atm, into the oxygen enrichment device, the dissolved oxygen concentration at 25° C. in the culture medium was 16 ppm in the case of the polyamide membrane and 14 ppm in the case of the polyester membrane.

0.55 mm were prepared from the polyamide and the polyester used in Example 30. Oxygen enrichment devices manufactured from these membranes in such a manner that fifteen hollow fiber were bound in a length of 750 mm and were dipped in culture vessels containing 500 ml of the same MS culture medium used in Example 30 and having a liquid surface area of 38 cm² and, after high pressure steam sterilizing at 127° C. for 30 minutes, ambient air was introduced into the device at 25° C. for two weeks. The dissolved oxygen concentration in the culture medium were determined. The results are shown in Table 11. In Table 11, the pressure of air introduced into the inside of the hollow fiber membrane and the dissolved oxygen concentration are shown. Furthermore, the evaporation loss of the culture medium was less than 1% even after 2 weeks.

TABLE 11

| Example | Base material of hollow fiber membrane | Air pressure (atm) | Dissolved oxygent conc. (ppm) | | |
|---|---|---|---|---|---|
| | | | 1 hr | 2 hr | Steady state |
| 31 | Polyamide | 1.5 | 8.5 | 9.5 | 11.5 |
| 32 | " | 2.0 | 9.0 | 10.0 | 12.0 |
| 33 | " | 3.0 | 10.5 | 12.0 | 12.5 |
| 34 | Polyester | 2.0 | 8.5 | 9.5 | 11.5 |

COMPARATIVE EXAMPLE 3

Air was bubbled into the cell culture vessel used in Examples 31 to 34 at a flow rate of 30 cm³/min. As a result, the dissolved oxygen concentration at a steady state was 8 ppm at 25° C. and the culture medium was lost by evaporation at a rate of about 10 ml/day.

Compared with the results of Examples 31 to 34, it is clear that the higher dissolved oxygen concentration in the culture medium can be obtained and the evaporation loss of the culture medium can be remarkably suppressed according to the present invention.

EXAMPLE 35

Under the same conditions as used in Example 31, 2 g of callus of carrot was subjected to cell cultivation. As a result, there was no contamination by microorganisms, and the callus weight was increased by about 3-fold two weeks after the initiation of cultivation. Also, the lowering in liquid level accompanying an evaporation loss of the culture medium, and cell adhesion at the interface between the liquid surface and the vessel wall, were alleviated.

EXAMPLE 36

Twenty hollow fibers with an outer diameter of 0.7 mm and an inner diameter of 0.5 mm comprising a polyamide having the above-mentioned structure (A-1) were arranged around a 1/16 inch stainless steel tube, and fixed within the bonding portion made of stainless steel with a thermosetting epoxy resin, to prepare a liquid dip type oxygen enrichment aeration device with a 1.2 m oxygen enrichment effective length deformed into a spiral shape and fixed to a glass cultivator containing 2 liters of pure water equipped with a stirrer and a dissolved oxygen concentration measuring device by the method shown in FIG. 4, to assemble a simulated culturing device, and said device was maintained at a constant temperature of 40° C.

When air pressurized to 3 atm. (gauge) was introduced into the present liquid type oxygen enrichment aeration device at $6 \times 10^{-3}$ Nm$^3$/hour, 10 ppm of dissolved oxygen concentration was obtained. By using the liquid dip type oxygen enrichment aeration device of the present invention, a higher value than the dissolved oxygen concentration attained by bubble aeration with ambient air (6.5 ppm at 40° C.) was obtained.

EXAMPLE 37

The hollow fibers portion of the oxygen enrichment aeration device shown in Example 36 was protected with a porous tube made of polytetrafluoroethylene with a maximum pore diameter of 3.5 μm, and the liquid dip type oxygen enrichment aeration device having the same constitution as in FIG. 5 was fixed to a glass cultivation tank containing 2 liters of MS culture medium to be used for plant callus cultivation, and after a high pressure steam sterilization treatment at 123° C. for one hour, callus of carrot was thrown therein, followed by a continuation of cultivation under the conditions of 25° C., 3 atm. of air pressure introduced (gauge), and an air flow rate of $6 \times 10^{-3}$ Nm$^3$/hour. The dissolved oxygen concentration in the culture broth was maintained at 12 ppm, and the callus amount was increased to 6-fold. Attachment of the callus to the hollow fibers was prevented by the porous tube.

We claim:

1. A separation membrane consisting of a polyester having a repeating unit (III):

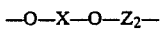
—O—X—O—Z$_2$—     (III)

wherein X represents

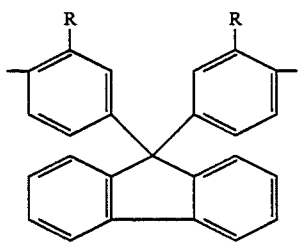

where R represents H, CH$_3$, or C$_2$H$_5$; and Z$_2$ represents the following structure:

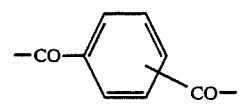

2. A separation membrane consisting of a polyester of (a) a unit (III):

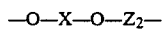
—O—X—O—Z$_2$—     (III)

where X represents

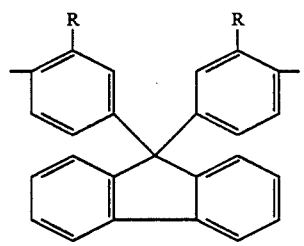

where R represents H, CH$_3$, or C$_2$H$_5$; and Z$_2$ represents the following structure:

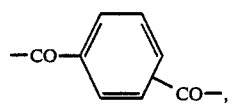

and (b) units (IV) and (IV'):

—(O—X—O—Z$_2$)$_r$—     (IV)

O—X—O—Z$_2$')$_s$—     (IV')

wherein X and Z$_2$ are the same as defined above and Z$_2$' represents —CO—CH=CH—CO—, and a ratio r/s is 0.05 to 100.

3. A gas permeation membrane consisting of the polyester of claim 1 or 2 wherein said membrane has a substantially uniform thickness of 20 μm or less and no micropores having a size of 1 nm or more.

* * * * *

UNITED STATES PATENT AND TRADEMARK OFFICE
CERTIFICATE OF CORRECTION

PATENT NO. : 4,968,331

DATED : November 6, 1990

INVENTOR(S) : M. Sakashita et al.

It is certified that error appears in the above-identified patent and that said Letters Patent is hereby corrected as shown below:

```
Column 28:
In claim 2 for unit (IV) change ")" to -- } --.

In claim 2 for unit (IV') before first "O" insert -- { --.
```

Signed and Sealed this

Twenty-second Day of September, 1992

*Attest:*

DOUGLAS B. COMER

*Attesting Officer*   *Acting Commissioner of Patents and Trademarks*